United States Patent
Rao et al.

(10) Patent No.: US 8,017,817 B2
(45) Date of Patent: Sep. 13, 2011

(54) PROCESS FOR THE PREPARATION OF 1,1,3,3,3-PENTAFLUOROPROPENE AND 1,2,3,3,3-PENTAFLUOROPROPENE

(75) Inventors: Velliyur Nott Mallikarjuna Rao, Wilmington, DE (US); H. David Rosenfeld, Drumore, PA (US); Allen Capron Sievert, Elkton, MD (US); Shekhar Subramoney, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 320 days.

(21) Appl. No.: 11/988,257

(22) PCT Filed: Aug. 4, 2006

(86) PCT No.: PCT/US2006/030530
§ 371 (c)(1), (2), (4) Date: Aug. 28, 2009

(87) PCT Pub. No.: WO2007/019354
PCT Pub. Date: Feb. 15, 2007

(65) Prior Publication Data
US 2011/0105808 A1  May 5, 2011

Related U.S. Application Data

(60) Provisional application No. 60/706,158, filed on Aug. 5, 2005.

(51) Int. Cl.
*C07C 7/00* (2006.01)
(52) U.S. Cl. .................... 570/156; 570/169
(58) Field of Classification Search .............. 570/156, 570/169
See application file for complete search history.

(56) References Cited

U.S. PATENT DOCUMENTS

| | | | |
|---|---|---|---|
| 6,031,141 A | 2/2000 | Mallikarjuna et al. | |
| 7,074,973 B2 | 7/2006 | Nappa et al. | |
| 7,129,383 B2 | 10/2006 | Nappa et al. | |
| 7,217,678 B2 | 5/2007 | Rao et al. | |
| 7,285,690 B2 | 10/2007 | Rao et al. | |
| 7,285,691 B2 | 10/2007 | Rao et al. | |
| 7,285,692 B2 | 10/2007 | Rao et al. | |
| 7,435,700 B2 | 10/2008 | Amos et al. | |
| 2005/0227865 A1 | 10/2005 | Nappa et al. | |
| 2009/0043138 A1 | 2/2009 | Rao et al. | |

FOREIGN PATENT DOCUMENTS

| | | |
|---|---|---|
| WO | WO 2005/037742 | 4/2005 |
| WO | WO2007/019353 | 2/2007 |
| WO | WO2007/019355 | 2/2007 |
| WO | WO2007/019356 | 2/2007 |
| WO | WO2007/019357 | 2/2007 |
| WO | WO2007/019358 | 2/2007 |
| WO | WO2007/019359 | 2/2007 |

OTHER PUBLICATIONS

U.S. Appl. No. 11/988,256, filed Feb. 15, 2007, Rao et al.
U.S. Appl. No. 11/988,436, filed Feb. 15, 2007, Rao et al.
U.S. Appl. No. 11/988,259, filed Feb. 15, 2007, Rao et al.
U.S. Appl. No. 11/988,258, filed Feb. 15, 2007, Rao et al.
U.S. Appl. No. 11/988,200, filed Feb. 15, 2007, Rao et al.
U.S. Appl. No. 11/988,983, filed Feb. 15, 2007, Rao et al.

*Primary Examiner* — Jafar Parsa

(57) ABSTRACT

A process for the manufacture of $CF_3CH=CF_2$ and $CF_3CF=CHF$ is disclosed. The process involves (a) reacting HF and chlorine and at least one halopropene of the formula $CX_3CCl=CCIX$ (where each X is independently F or Cl) to produce a product including both $CF_3CCl_2CF_3$ and $CF_3CClFCClF_2$; (b) reacting $CF_3CCl_2CF_3$ and $CF_3CClFCClF_2$ produced in (a) with hydrogen to produce a product including both $CF_3CH_2CF_3$ and $CF_3CHFCHF_2$; (c) dehydrofluorinating $CF_3CH_2CF_3$ and $CF_3CHFCHF_2$ produced in (b) to produce a product including both $CF_3CH=CF_2$ and $CF_3CF=CHF$; and (d) recovering $CF_3CH=CF_2$ and $CF_3CF=CHF$ from the product produced in (c). In (a), both $CF_3CCl_2CF_3$ and $CF_3CClFCClF_2$ are produced in the presence of a chlorofluorination catalyst consisting of (i) compositions comprising a crystalline alpha-chromium oxide where at least 0.05 atom % of the chromium atoms in the alpha-chromium oxide lattice are replaced by copper, and (H) compositions of (i) which have been treated with a fluorinating agent.

4 Claims, No Drawings

PROCESS FOR THE PREPARATION OF 1,1,3,3,3-PENTAFLUOROPROPENE AND 1,2,3,3,3-PENTAFLUOROPROPENE

FIELD OF THE INVENTION

This invention relates to the synthesis 1,1,3,3,3-pentafluoropropene and 1,2,3,3,3-pentafluoropropene.

BACKGROUND

A number of chlorine-containing halocarbons are considered to be detrimental toward the Earth's ozone layer. There is a worldwide effort to develop materials having lower ozone depletion and global warming potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. HFC-134a has a high global warming potential. There is a need for manufacturing processes that provide halogenated hydrocarbons that have lower ozone depletion and global warming potential. The production of hydrofluoroolefins (i.e., unsaturated compounds containing only carbon, hydrogen and fluorine), has been the subject of recent interest to provide environmentally desirable products for use as refrigerants, solvents, blowing agents, cleaning agents, aerosol propellants, heat transfer media, dielectrics, fire extinguishants, power cycle working fluids and polymer intermediates. For example, 1,1,3,3,3-pentafluoropropene has utility as a monomer for producing various polymers and 1,2,3,3,3-pentafluoropropene has utility as a refrigerant.

SUMMARY OF THE INVENTION

This invention provides a process for the manufacture of 1,1,3,3,3-pentafluoropropene ($CF_3CH=CF_2$, HFC-1225zc) and 1,2,3,3,3-pentafluoropropene ($CF_3CF=CHF$, HFC-1225ye). The process comprises (a) reacting HF, $Cl_2$ and at least one halopropene of the formula $CX_3CCl=CClX$, wherein each X is independently selected from the group consisting of F and Cl, to produce a product comprising $CF_3CCl_2CF_3$ and $CF_3CClFCClF_2$, wherein said $CF_3CCl_2CF_3$ and $CF_3CClFCClF_2$ are produced in the presence of a chlorofluorination catalyst comprising at least one chromium-containing component selected from (i) a crystalline alpha-chromium oxide where at least 0.05 atom % of the chromium atoms in the alpha-chromium oxide lattice are replaced by divalent copper, and (ii) a chromium-containing composition of (i) which has been treated with a fluorinating agent (e.g., anhydrous hydrogen fluoride); (b) reacting $CF_3CCl_2CF_3$ and $CF_3CClFCClF_2$ produced in (a) with hydrogen ($H_2$), optionally in the presence of HF, to produce a product comprising $CF_3CH_2CF_3$ and $CF_3CHFCHF_2$; (c) dehydrofluorinating $CF_3CH_2CF_3$ and $CF_3CHFCHF_2$ produced in (b), to produce a product comprising $CF_3CH=CF_2$ and $CF_3CF=CHF$; and (d) recovering $CF_3CH=CF_2$ and $CF_3CF=CHF$ from the product produced in (c).

DETAILED DESCRIPTION

This invention provides a process for the preparation of $CF_3CH=CF_2$ (HFC-1225zc) and $CF_3CF=CHF$ (HFC-1225ye).

In step (a) of the process of this invention, one or more halopropene compounds $CX_3CCl=CClX$, wherein each X is independently selected from the group consisting of F and Cl, are reacted with chlorine ($Cl_2$) and hydrogen fluoride (HF) to produce a product mixture comprising $CF_3CCl_2CF_3$ (CFC-216aa) and $CF_3CClFCClF_2$ (CFC-216ba). Accordingly, this invention provides a process for the preparation of mixtures of $CF_3CCl_2CF_3$ (CFC-216aa) and $CF_3CClFCClF_2$ (CFC-216ba) from readily available starting materials.

Suitable starting materials for the process of this invention include E- and Z—$CF_3CCl=CClF$ (CFC-1214xb), $CF_3CCl=CCl_2$ (CFC-1213xa), $CClF_2CCl=CCl_2$ (CFC-1212xa), $CCl_2FCCl=CCl_2$ (CFC-1211xa), and $CCl_3CCl=CCl_2$ (hexachloropropene, HCP) or mixtures thereof.

Preferred starting materials for the process of this invention are $CF_3CCl=CCl_2$ (CFC-1213xa) and $CCl_3CCl=CCl_2$ (hexachloropropene, HCP) based on their ready accessibility.

Preferably, the reaction of HF and $Cl_2$ with the halopropenes $CX_3CCl=CClX$ is carried out in the vapor phase in a heated tubular reactor. A number of reactor configurations are possible including horizontal or vertical orientation of the reactor and different modes of contacting the halopropene starting materials with HF and chlorine. Preferably the HF and chlorine are substantially anhydrous.

In one embodiment of step (a) the halopropene starting material(s) are fed to the reactor containing the chlorofluorination catalyst. The halopropene starting material(s) may be initially vaporized and fed to the reactor as gas(es).

In another embodiment of step (a), the halopropene starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing of $CX_3CCl=CClX$ and HF vapor.

When liquid feed of the halopropene starting material(s) to the pre-reactor is used, it is preferable for the pre-reactor to be oriented vertically with $CX_3CCl=CClX$ entering the top of the reactor and pre-heated HF vapor introduced at the bottom of the reactor.

Suitable temperatures for the pre-reactor are within the range of from about 80° C. to about 250° C., preferably from about 100° C. to about 200° C. Under these conditions, for example, hexachloropropene is converted to a mixture containing predominantly CFC-1213xa. The feed rate of starting material is determined by the length and diameter of the pre-reactor, the pre-reactor temperature, and the degree of fluorination desired within the pre-reactor. Slower feed rates at a given temperature will increase contact time and tend to increase the amount of conversion of the starting material and increase the degree of fluorination of the products.

The term "degree of fluorination" means the extent to which fluorine atoms replace chlorine substituents in the $CX_3CCl=CClX$ starting materials. For example, $CF_3CCl=CClF$ represents a higher degree of fluorination than $CClF_2CCl=CCl_2$ and $CF_3CCl_2CF_3$ represents a higher degree of fluorination than $CClF_2CCl_2CF_3$.

The molar ratio of HF fed to the pre-reactor, or otherwise to the reaction zone of step (a), to halopropene starting material fed in step (a), is typically from about stoichiometric to about 50:1. The stoichiometric ratio depends on the average degree of fluorination of the halopropene starting material(s) and is typically based on formation of $C_3Cl_2F_6$. For example, if the halopropene is HCP, the stoichiometric ratio of HF to HCP is 6:1; if the halopropene is CFC-1213xa, the stoichiometric ratio of HF to CFC-1213xa is 3:1. Preferably, the ratio of HF to halopropene starting material is from about twice the stoichiometric ratio of HF to halopropene (based on formation of $C_3Cl_2F_6$) to about 30:1. Higher ratios of HF to halopropene are not particularly beneficial; lower ratios result in reduced yields of $C_3Cl_2F_6$.

If the halopropene starting materials are contacted with HF in a pre-reactor, the effluent from the pre-reactor is contacted with chlorine in the reaction zone of step (a).

In another embodiment of the invention, the halopropene starting material(s) may be contacted with $Cl_2$ and HF in a pre-reactor. The pre-reactor may be empty (i.e., unpacked), but is preferably filled with a suitable packing such as Monel™ or Hastelloy™ nickel alloy turnings or wool, activated carbon, or other material inert to HCl, HF, and $Cl_2$ which allows efficient mixing of $CX_3CCl=CClX$, HF, and $Cl_2$.

Typically at least a portion of the halopropene starting material(s) react(s) with $Cl_2$ and HF in the pre-reactor by addition of $Cl_2$ to the olefinic bond to give a saturated halopropane as well as by substitution of at least a portion of the Cl substituents in the halopropopane and/or halopropene by F. Suitable temperatures for the pre-reactor in this embodiment of the invention are within the range of from about 80° C. to about 250° C., preferably from about 100° C. to about 200° C. Higher temperatures result in greater conversion of the halopropene(s) entering the reactor to saturated products and a greater degree of halogenation of the starting material. In the presence of HF, the degree of fluorination will also increase at higher pre-reactor temperatures.

The term "degree of halogenation" means the extent to which hydrogen substituents in a halocarbon have been replaced by halogen and carbon-carbon double bonds have been saturated with halogen. For example, $CF_3CCl_2CClF_2$ has a higher degree of halogenation than $CF_3CCl=CCl_2$. Also, $CF_3CClFCF_3$ has a higher degree of halogenation than $CF_3CHClCF_3$.

The molar ratio of $Cl_2$ fed to the pre-reactor, or otherwise to the reaction zone of step (a), to halopropene starting material(s) fed in step (a), is typically from about 1:1 to about 10:1. Feeding $Cl_2$ at less than a 1:1 ratio will result in the presence of relatively large amounts of unsaturated materials and hydrogen-containing side products in the reactor effluent.

In a preferred embodiment of step (a), the halopropene starting materials are vaporized, preferably in the presence of HF, and contacted with HF and $Cl_2$ in a pre-reactor and then contacted with the chlorofluorination catalyst. If the preferred amounts of HF and $Cl_2$ are fed in the pre-reactor, additional HF and $Cl_2$ are not required in the reaction zone.

Suitable temperatures in the reaction zone(s) of step (a) are within the range of from about 230° C. to about 425° C., preferably from about 250° C. to about 400° C. Higher temperatures result in greater conversion of the $CX_3CCl=CClX$ starting materials, but also result in formation of overfluorinated products such as $CF_3CClFCF_3$ and contribute to reduced catalyst life. As illustrated in the Examples, the preferred temperature range is somewhat dependent on the activity of the catalyst. Temperatures lower than about 250° C. result in low yields of CFC-216aa and CFC-216ba. Unconverted starting materials and products having a degree of fluorination lower than six may be recycled back to the reaction zone.

Suitable reactor pressures for vapor phase embodiments of this invention may be in the range of from about 1 to about 30 atmospheres. Reactor pressures of about 5 atmospheres to about 20 atmospheres may be advantageously employed to facilitate separation of HCl from other reaction products.

The chlorofluorination catalysts which are used in the process of the present invention are compositions comprising crystalline $\alpha$-$Cr_2O_3$ ($\alpha$-chromium oxide) in which some of the chromium(III) ions have been substituted by copper(II) ions or compositions obtained by treatment of said compositions with a fluorinating agent. Of note are embodiments containing at least 1 atom % copper based on the total of the copper and chromium in the alpha-chromium oxide. The amount of copper relative to the total of chromium and copper in these compositions is preferably from about 1 atom % to about 5 atom %. Of particular note are embodiments containing from about 2 atom % to about 3 atom % copper based on the total of the copper and chromium in the alpha-chromium oxide.

These compositions may be prepared, for example, by co-precipitation methods followed by calcination.

In a typical co-precipitation procedure, an aqueous solution of copper and chromium(III) salts is prepared. The relative concentrations of the copper and chromium(III) salts in the aqueous solution is dictated by the bulk atom percent copper relative to chromium desired in the final catalyst. Therefore, the concentration of copper in the aqueous solution is from about 1 atom % to about 5 atom % of the total concentration of copper and chromium in the solution. The concentration of chromium(III) in the aqueous solution is typically in the range of 0.3 to 3 moles per liter with 0.75-1.5 moles per liter being a preferred concentration. While different chromium(III) salts might be employed, chromium(III) nitrate or its hydrated forms such as $[Cr(NO_3)_3(H_2O)_9]$, are the most preferred chromium(III) salts for preparation of said aqueous solution.

While different copper salts might be employed for preparation of said aqueous solutions, preferred copper salts for preparation of catalysts for the process of this invention include copper(II) nitrate and its hydrated forms such as $[Cu(NO_3)_2(H_2O)_{2.5}]$ and copper(II) chloride.

The aqueous solution of the chromium(III) and copper salts may then be evaporated either under vacuum or at elevated temperature to give a solid which is then calcined.

It is preferred to treat the aqueous solution of the chromium(III) and copper salts with a base such as ammonium hydroxide (aqueous ammonia) to precipitate the copper and chromium as the hydroxides. Bases containing alkali metals such as sodium or potassium hydroxide or the carbonates may be used but are not preferred. The addition of ammonium hydroxide to the aqueous solution of the chromium(III) and copper salts is typically carried out gradually over a period of 1 to 12 hours. The pH of the solution is monitored during the addition of base. The final pH is typically in the range of 6.0 to 11.0, preferably from about 7.5 to about 9.0, most preferably about 8.0 to about 8.7. The precipitation of the copper and chromium hydroxide mixture is typically carried out at a temperature of about 15° C. to about 60° C., preferably from about 20° C. to about 40° C. After the ammonium hydroxide is added, the mixture is typically stirred for up to 24 hours. The precipitated chromium and copper hydroxides serve as precursors to the catalysts of the invention After the precipitation of the copper and chromium hydroxide mixture is complete, the mixture is dried. This may be carried out by evaporation in an open pan on a hot plate or steam bath or in an oven or furnace at a suitable temperature. Suitable temperatures include temperatures from about 60° C. to about 130° C. (for example, about 100° C. to about 120° C.). Alternatively, the drying step may be carried out under vacuum using, for example, a rotary evaporator.

Optionally, the precipitated copper and chromium hydroxide mixture may be collected and, if desired, washed with deionized water before drying. Preferably the precipitated copper and chromium hydroxide mixture is not washed prior to the drying step.

After the copper and chromium hydroxide mixture has been dried, the nitrate salts are then decomposed by heating the solid from about 250° C. to about 350° C. The resulting solid is then calcined at temperatures of from about 400° C. to about 1000° C., preferably from about 400° C. to about 900° C.

The copper-substituted alpha-chromium oxide compositions may also be prepared by a thermal method. In this method, a solution of the copper and chromium(III) salts is prepared as described for the co-precipitation technique. The mixed solution of the salts is then evaporated under atmospheric pressure or reduced pressure to give a solid. The solid is then placed in a furnace and the temperature raised gradually to decompose the salt. It is preferred to use the nitrate salts that decompose to the oxide. After decomposition of the nitrate salts is complete (about 350° C.), the increase in temperature is continued until the desired calcination temperature is reached. The desired calcination temperature is between about 450° C. to about 1000° C., a temperature of about 450° C. to about 900° C. being preferred. After the desired calcination temperature is reached, the solid is maintained at this temperature for an additional 8 to 24 hours, about 8 to about 12 hours being preferred. The decomposition and calcination is preferably carried out in the presence of oxygen, most preferably in the presence of air.

Further information on the copper and chromium compositions useful for this invention is provided in U.S. Patent Application 60/706,159 filed Aug. 5, 2005, and hereby incorporated by reference herein in its entirety.

The calcined copper-substituted alpha-chromium oxide compositions used in the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pretreatment is not essential.

Compounds that are produced in the chlorofluorination process in step (a) include the halopropanes $CF_3CCl_2CF_3$ (CFC-216aa) and $CF_3CClFCClF_2$ (CFC-216ba).

Halopropane by-products that have a higher degree of fluorination than CFC-216aa and CFC-216ba that may be produced in step (a) include $CF_3CClFCF_3$ (CFC-217ba) and $CF_3CF_2CF_3$ (FC-218).

Halopropane and halopropene by-products that may be formed in step (a) which have lower degrees of fluorination and/or halogenation than CFC-216aa and CFC-216ba include $CF_3CCl_2CClF_2$ (CFC-215aa), $CF_3CClFCCl_2F$ (CFC-215bb), $CF_3CCl_2CCl_2F$ (CFC-214ab), and $CF_3CCl=CF_2$ (CFC-1215xc).

Prior to step (b), $CF_3CCl_2CF_3$ and $CF_3CClFCClF_2$, (and optionally HF) in the effluent from the reaction zone in step (a), are typically separated from the low boiling components of the effluent (which typically comprise HCl, $Cl_2$, HF, and over-fluorinated products such as $CF_3CClFCF_3$) and the under-fluorinated components of the effluent (which typically comprise $C_3Cl_3F_5$ isomers, $C_3Cl_4F_4$ isomers, and/or under-halogenated components such as $C_3Cl_2F_4$ isomers and $CF_3CCl=CCl_2$). The higher boiling components may be returned to step (a).

In one embodiment of this invention, the under-fluorinated components CFC-215aa and CFC-215bb may be converted to $CF_3CH_2CHF_2$ (HFC-245fa) and $CF_3CHFCH_2F$ (HFC-245eb) as disclosed in U.S. Patent Application 60/706,162 filed Aug. 5, 2005.

In another embodiment of this invention, the reactor effluent from step (a) is delivered to a distillation column in which HCl and any HCl azeotropes are removed from the top of the column while the higher boiling components are removed from the bottom of the column. The products recovered from the bottom of the first distillation column are then delivered to a second distillation column in which HF, $Cl_2$, and any CFC-217ba are recovered at the top of the second distillation column and remaining HF and organic products, comprising $CF_3CCl_2CF_3$ and $CF_3CClFCClF_2$, are recovered at the bottom of the distillation column. The products recovered from the bottom of the second distillation column may be delivered to further distillation columns or may be delivered to a decanter controlled at a suitable temperature to permit separation of an organic-rich phase and an HF-rich phase. The HF-rich phase may be distilled to recover HF that is then recycled to step (a). The organic-rich phase may then be delivered to step (b).

In step (b) of the process, the $CF_3CCl_2CF_3$ and $CF_3CClFCClF_2$ produced in step (a) are reacted with hydrogen ($H_2$), optionally in the presence of HF, in a second reaction zone.

In one embodiment of step (b), the reacting of hydrogen with the CFC-216aa/ba mixture produced in step (a), and optionally HF, is carried out in a reaction zone in the presence of a hydrogenation catalyst. Hydrogenation catalysts suitable for use in this embodiment include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite. The hydrogenolysis of saturated acyclic halofluorocarbons containing 3 or 4 carbon atoms using palladium supported on carbon is disclosed in U.S. Pat. No. 5,523,501, the teachings of which are incorporated herein by reference.

Of note are carbon supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference.

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industrial Practice,* 2nd edition (McGraw-Hill, New York, 1991). The concentration of the catalytic metal(s) on the support is typically in the range of about 0.1% by weight of the catalyst to about 5% by weight.

Suitable temperatures for the reaction zone containing said hydrogenation catalyst are in the range of from about 100° C. to about 400° C., preferably from about 125° C. to about 350° C. Higher temperatures typically result in greater conversion of CFC-216aa and CFC-216ba with fewer partially chlorinated intermediates such as $C_3HClF_6$ isomers. At reaction zone temperatures in the range of 125° C. to 300° C. the primary products of the hydrodechlorination process are HFC-236fa and HFC-236ea.

Temperatures above about 400° C. may cause hydrogenolysis of carbon-fluorine and carbon-carbon bonds; temperatures lower than about 125° C. may result in low conversion of the halopropanes and the formation of large amounts of partially chlorinated intermediates.

The amount of hydrogen ($H_2$) fed to the reaction zone containing said hydrogenation catalyst is typically from about 1 mole of $H_2$ per mole of dichlorohexafluoropropane to about 20 moles of $H_2$ per mole of dichlorohexafluoropropane, preferably from about 2 moles of $H_2$ per mole of dichlorohexafluoropropane to about 10 moles of $H_2$ per mole of dichlorohexafluoropropane.

The pressure used in the step (b) reaction zone is not critical and may be in the range of from about 1 to 30 atmospheres. A pressure of about 20 atmospheres may be advantageously employed to facilitate separation of HCl from other reaction products.

The effluent from the step (b) reaction zones typically includes HCl, $CF_3CH_2CF_3$ (HFC-236fa), $CF_3CHFCHF_2$ (HFC-236ea), and small amounts of lower boiling products (typically including propane, $CF_3CH=CF_2$ (HFC-1225zc), and higher boiling products and intermediates (typically including $C_3HClF_6$ isomers) as well as any unconverted starting materials and any HF carried over from step (a). The HFC-236fa and HFC-236ea are typically separated from the lower boiling products and higher boiling products by conventional means (e.g., distillation).

In step (c) of the process, $CF_3CH_2CF_3$ and $CF_3CHFCHF_2$ produced in step (b) are dehydrofluorinated.

In one embodiment of step (c), a mixture comprising $CF_3CH_2CF_3$ and $CF_3CHFCHF_2$, and optionally an inert gas, is delivered in the vapor phase to a dehydrofluorination catalyst as described in U.S. Pat. No. 6,369,284; the teachings of this disclosure are incorporated herein by reference. Dehydrofluorination catalysts suitable for use in this embodiment include (1) at least one compound selected from the oxides, fluorides and oxyfluorides of magnesium, zinc and mixtures of magnesium and zinc, (2) lanthanum oxide, (3) fluorided lanthanum oxide, (4) activated carbon, and (5) three-dimensional matrix carbonaceous materials.

The catalytic dehydrofluorination of $CF_3CH_2CF_3$ and $CF_3CHFCHF_2$ is suitably conducted at a temperature in the range of from about 200° C. to about 500° C., and preferably from about 350° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $CF_3CH_2CF_3$ and $CF_3CHFCHF_2$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $CF_3CH_2CF_3$ and/or $CF_3CHFCHF_2$ is from about 5:1 to 1:1. Nitrogen is the preferred inert gas.

The products from the step (c) reaction zone typically include HF, $CF_3CH=CF_2$, E- and Z—$CF_3CF=CHF$, and small amounts of other products. Unconverted $CF_3CH_2CF_3$ and $CF_3CHFCHF_2$ are recycled back to the dehydrofluorination reactor to produce additional quantities of $CF_3CH=CF_2$ and E/Z—$CF_3CF=CHF$.

In another embodiment of step (c), the $CF_3CH_2CF_3$ and $CF_3CHFCHF_2$ are subjected to dehydrofluorination at an elevated temperature in the absence of a catalyst as disclosed in U.S. Patent Application No. 60/623,210 filed Oct. 29, 2004, which is incorporated herein by reference. The reactor can be fabricated from nickel, iron, titanium, or their alloys, as described in U.S. Pat. No. 6,540,933; the teachings of this disclosure are incorporated herein by reference. A reaction vessel of these materials (e.g., a metal tube) optionally packed with the metal in suitable form may also be used. When reference is made to alloys, it is meant a nickel alloy containing form 1 to 99.9% (by weight) nickel, an iron alloy containing 0.2 to 99.8% (by weight) iron, and a titanium alloy containing 72-99.8% (by weight) titanium. Of note is use of an empty (unpacked) reaction vessel made of nickel or alloys of nickel such as those containing 40% to 80% nickel, e.g., Inconel™ 600 nickel alloy, Hastelloy™ C617 nickel alloy, or Hastelloy™ C276 nickel alloy.

Also of note is a reaction vessel where the reaction zone is lined with mechanically supported nickel as disclosed in U.S. Patent Application Publication No. US 2005/0137430 A1 where the nickel is present in the reaction zone as a lining that is mechanically supported by a backing metal material of construction that provides the strength and ductility for fabrication of the reaction zone and its use, the teachings of which are incorporated herein by reference.

When used for packing, the metal or metal alloys may be particles or formed shapes such as perforated plates, rings, wire, screen, chips, pipe, shot, gauze, or wool.

The temperature of the reaction in this embodiment can be between about 350° C. and about 900° C., and is preferably at least about 450° C.

In yet another embodiment of step (c), the $CF_3CH_2CF_3$ and $CF_3CHFCHF_2$ are dehydrofluorinated by reaction with caustic (eg. KOH). The vapor-phase dehydrofluorination reaction of $CF_3CHFCHF_2$ with caustic to produce both $CF_3CH=CF_2$ and $CF_3CF=CHF$ is disclosed by Sianesi, et. al., *Ann. Chim.*, 55, 850-861 (1965) and the liquid-phase dehydrofluorination reaction of $CF_3CHFCHF_2$ and other hydrofluorocarbons in di-n-butyl ether using caustic is disclosed by Knunyants, et. al., *Izv. Akad. Nauk. SSSR*, 1960, pp. 1412-1418, *Chem. Abstracts* 55, 349f the teachings of which are incorporated herein by reference.

In step (d) of the process, the $CF_3CH=CF_2$ and $CF_3CF=CHF$ produced in (c) are recovered by well-known procedures such as distillation.

The reactor, distillation columns, and their associated feed lines, effluent lines, and associated units used in applying the processes of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

Catalyst Preparations

Comparative Preparation Example 1

Preparation of 100% Chromium Catalyst

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The dried solid was then calcined in air at 400° C.; the resulting solid weighed 61.15 g. The catalyst was pelletized (−12 to +20 mesh, 1.68 to 0.84 mm)) and 28.2 g (20 mL) was used in Comparative Example 1.

Preparation Example 1

Preparation of 99% Chromium/1% Copper Catalyst

To a one liter beaker containing 261.0 g $Cr(NO_3)_3[9(H_2O)]$ (0.652 mole) and 1.46 g $Cu(NO_3)_2[2.5\ H_2O]$ 0.0063 mole) was added 100 mL of deionized water. The slurry was placed on a stirring hot plate in a fume-hood and heated while stirring until oxides of nitrogen started to evolve. The beaker containing the paste-like material was placed in a furnace in the fume-hood after removing the stirrer. The temperature of the furnace was raised to 150° C. at the rate of 10 degrees/min and then to 550° C. at the rate of 1 degree/minute. It was held at 550° C. for an additional 10 hours. The resulting solid was pelletized (−12 to +20 mesh, 1.68 to 0.84 mm)) and 12.6 g (8.0 mL) was used in Example 1.

Preparation Example 2

Preparation of 99% Chromium/1% Copper Catalyst

In a 2000 mL beaker was placed 400.2 g $Cr(NO_3)_3[9(H_2O)]$ (1.0 mole) and 1.64 g $CuCl_2$ (0.012 mole). To the solids was added 1000 mL of deionized water. The mixture was stirred and when the dissolution was complete, the pH of the solution was raised from 2.0 to 8.0 by drop-wise addition of 8 molar aqueous ammonium hydroxide. The precipitated slurry was stirred for 24 hours at room temperature. It was then dried at 120-130° C. overnight and calcined at 450° C. for an additional 24 hours in air. The resulting solid was pelletized (−12 to +20 mesh, 1.68 to 0.84 mm)) and 11.0 g (8.0 mL) was used in Example 2.

Preparation Example 3

Preparation of 99% Chromium/1% Copper Catalyst

In a 3000 mL beaker was placed 500.0 g $Cr(NO_3)_3[9(H_2O)]$ (1.25 moles) and 3.05 g $Cu(NO_3)_2[2.5\ H_2O$ (0.013 mole). To the solids was added 1200 mL of deionized water. The mixture was stirred and when the dissolution was complete, the pH of the solution was raised from 2.4 to 8.5 by drop-wise addition of 300 mL of 8 molar aqueous ammonium hydroxide. The precipitated slurry was stirred for 24 hours at room temperature. It was then dried at 110-120° C. overnight and calcined at 500° C. for an additional 24 hours in air. The resulting solid was pelletized (−12 to +20 mesh, 1.68 to 0.84 mm)) and 16.0 g (8.0 mL) was used in Example 3.

Preparation Example 4

Preparation of 98% Chromium/2% Copper Catalyst

Preparation Example 1 was substantially repeated except that the amount of chromium(III) nitrate was 258.0 g (0.645 mole) and the amount of copper (II) nitrate was 2.9 g (0.0125 mole). The resulting solid was pelletized (−12 to +20 mesh, 1.68 to 0.84 mm)) and 12.6 g (8.0 mL) was used in Example 4.

Preparation Example 5

Preparation of 98% Chromium/2% Copper Catalyst

Preparation Example 2 was substantially repeated with 400.2 g chromium(III) nitrate (1.0 mole) and 3.31 g (0.0246 mole) copper(II) chloride. The solid, calcined in air at 450° C. for 24 hours, was pelletized (−12 to +20 mesh, 1.68 to 0.84 mm)) and 10.9 g (8.0 mL) was used in Example 5.

Preparation Example 6

Preparation of 98% Chromium/2% Copper Catalyst

In a 3000 mL beaker was placed 500.0 g $Cr(NO_3)_3[9(H_2O)]$ (1.1.25 mole) and 6.1 g $Cu(NO_3)_2[2.5\ H_2O]$ (0.0262 mole). To the solids was added 1200 mL of deionized water. The mixture was stirred and when the dissolution was complete, the pH of the solution was raised from 2.4 to 8.2 by drop-wise addition of 300 mL 8 molar aqueous ammonium hydroxide. The precipitated slurry was stirred for 24 hours at room temperature. It was then dried at 110-120° C. overnight and calcined at 500° C. for an additional 24 hours in air. The resulting solid was pelletized (−12 to +20 mesh, 1.68 to 0.84 mm)) and 14.9 g (8.0 mL) was used in Example 6 as the catalyst.

Preparation Example 7

Preparation of 95% Chromium/5% Copper Catalyst

Preparation Example 1 was substantially repeated except that the amount of chromium(III) nitrate was 250.0 g (0.625 mole) and the amount of copper(II) nitrate was 7.3 g (0.314 mole). The resulting solid was calcined at 550° C. overnight, pelletized (−12 to +20 mesh, 1.68 to 0.84 mm)) and 11.9 g (8.0 mL) was used in Example 7.

Preparation Examples 8-9

Preparation of 95% Chromium/5% Copper Catalyst

Preparation Example 6 was substantially repeated except that the amounts of chromium(III) nitrate and copper(II) nitrate were adjusted to produce a catalyst having a ratio of chromium to copper of 95/5. The solid dried at 110-120° C. overnight was divided into two portions. One portion was calcined at 500° C. and another portion was calcined at 900° C. A 35.8 g (25.0 ml) portion, calcined at 500° C. and pelletized to −12 to +20 mesh, was used in Example 8. Similarly a 48.1 g (25.0 ml) portion, calcined at 900° C. and pelletized to −12 to +20 mesh (1.68 to 0.84 mm), was used in Example 9.

Examples 1-9 and Comparative Example 1

General Procedure for Chlorofluorination

A weighed quantity of pelletized catalyst was placed in a 5/8 inch (1.58 cm) diameter Inconel™ nickel alloy reactor tube heated in a fluidized sand bath. The tube was heated from 50° C. to 175° C. in a flow of nitrogen (50 cc/min; $8.3(10)^{-7}$ m³/sec) over the course of about one hour. HF was then admitted to the reactor at a flow rate of 50 cc/min $(8.3(10)^{-7}$ m³/sec). After 0.5 to 2 hours the nitrogen flow was decreased to 20 cc/min (3.3(10)⁻⁷ m³/sec) and the HF flow increased to 80 cc/min (1.3(10)⁻⁶ m³/sec); this flow was maintained for about 1 hour. The reactor temperature was then gradually increased to 400° C. over 3 to 5 hours. At the end of this period, the HF flow was stopped and the reactor cooled to 300° C. under 20 sccm (3.3(10)⁻⁷ m³/sec) nitrogen flow. CFC-1213xa was fed from a pump to a vaporizer maintained at about 118° C. It was combined with the appropriate molar ratios of HF and chlorine in a 0.5 inch (1.27 cm) diameter Monel™ nickel alloy tube packed with Monel™ turnings. The mixture of reactants then entered the reactor. The HF/1213xa/chlorine molar ratio was 20/1/4 for all runs and the contact time was 5 seconds for Examples 1-7, 30 seconds for Examples 8-9 and 20 seconds for Comparative Example 1. The reactions were conducted at a nominal pressure of one atmosphere. Analytical data for identified compounds is given in units of GC area %. Small quantities of other unidentified products were present.

General Procedure for Fluorocarbon Product Analysis

The following general procedure is illustrative of the method used for analyzing the products of the chlorofluorination reactions. Part of the total reactor effluent was sampled on-line for organic product analysis using a gas chromatograph equipped a mass selective detector (GC-MS). The gas chromatography was accomplished with a 20 ft. (6.1 m) long×⅛ in. (0.32 cm) diameter tubing containing Krytox® perfluorinated polyether on an inert carbon support. The helium flow was 30 mL/min (5.0(10)⁻⁷ m³/sec). Gas chromatographic conditions were 60° C. for an initial hold period of three minutes followed by temperature programming to 200° C. at a rate of 6° C./minute.

| Legend | |
|---|---|
| 214ab is $CF_3CCl_2CCl_2F$ | 215aa is $CF_3CCl_2CClF_2$ |
| 215bb is $CCl_2FCClFCF_3$ | 216aa is $CF_3CCl_2CF_3$ |
| 216ba is $CClF_2CClFCF_3$ | 216cb is $CCl_2FCF_2CF_3$ |
| 217ba is $CF_3CClFCF_3$ | 217ca is $CF_3CF_2CClF_2$ |
| 225da is $CF_3CHClCClF_2$ | 226da is $CF_3CHClCF_3$ |
| 1214 is $C_3Cl_2F_4$ | 1215xc is $CF_3CCl\!=\!CF_2$ |

Chlorofluorination of 1213xa

The chlorofluorination of CFC-1213xa was carried out at various temperatures using catalysts prepared according to Catalyst Preparation Examples 1-9. The analytical results shown in Table 1 are reported as GC area %.

TABLE 1

| Ex. No. | Cat Prep. | T °C. | 217ba | 217ca | 1215xc | 226da | 216aa | 216ba | 216cb | 215aa | 215bb | 214ab | 1214 |
|---|---|---|---|---|---|---|---|---|---|---|---|---|---|
| 1 | 1 | 280 | 0.7 | ND | 0.9 | 2.4 | 14.4 | 4.8 | 0.6 | 63.4 | 8.5 | 3.2 | 0.3 |
| | | 320 | 3.4 | 0.3 | 1.0 | 2.4 | 36.3 | 14.8 | 1.2 | 38.9 | 1.4 | ND | ND |
| | | 375 | 5.8 | 1.3 | 0.3 | 1.4 | 60.2 | 13.7 | 0.4 | 16.7 | ND | ND | ND |
| 2 | 2 | 280 | 0.4 | ND | 0.4 | 1.4 | 13.2 | 7.6 | 0.8 | 61.0 | 13.8 | ND | ND |
| | | 320 | 1.4 | 0.4 | 0.2 | 1.4 | 31.1 | 23.3 | 1.0 | 41.1 | 0.1 | ND | ND |
| | | 375 | 3.2 | 1.2 | 0.1 | 0.8 | 59.3 | 16.7 | 0.2 | 18.4 | 0.1 | ND | ND |
| 3 | 3 | 320 | 2.4 | 0.4 | 0.3 | 0.8 | 32.8 | 26.6 | 2.0 | 33.5 | 1.1 | ND | ND |
| | | 350 | 2.9 | 1.1 | 0.3 | 0.5 | 42.3 | 26.5 | 1.4 | 24.8 | ND | ND | ND |
| | | 375 | 3.4 | 1.6 | 0.1 | 0.5 | 53.6 | 21.8 | 0.5 | 18.5 | ND | ND | ND |
| 4 | 4 | 280 | 0.2 | ND | 1.7 | 0.4 | 11.0 | 2.3 | 1.4 | 26.5 | 33.6 | 18.2 | 4.7 |
| | | 320 | 0.4 | ND | 0.9 | 0.5 | 21.0 | 12.1 | 1.9 | 41.8 | 20.4 | 0.8 | 0.1 |
| | | 350 | 0.5 | 0.2 | 0.6 | 0.4 | 28.1 | 21.2 | 2.5 | 36.8 | 9.4 | 0.1 | ND |
| 5 | 5 | 350 | 0.2 | 0.2 | 0.2 | 0.2 | 18.4 | 28.8 | 1.7 | 45.5 | 4.7 | ND | ND |
| | | 375 | 0.3 | 0.5 | 0.2 | 0.1 | 24.4 | 30.6 | 1.6 | 41.4 | 0.7 | ND | ND |
| | | 400 | 0.6 | 0.9 | 0.2 | 0.1 | 31.5 | 28.5 | 1.2 | 36.7 | 0.2 | ND | ND |
| 6 | 6 | 320 | 0.3 | 0.2 | 0.2 | 0.2 | 16.3 | 27.7 | 2.4 | 41.7 | 10.3 | ND | ND |
| | | 350 | 0.9 | 0.8 | 0.3 | 0.2 | 26.7 | 33.1 | 2.0 | 33.9 | 2.0 | ND | ND |
| | | 375 | 2.2 | 1.8 | 0.1 | 0.1 | 44.3 | 28.4 | 0.8 | 21.8 | 0.4 | ND | ND |
| 7 | 7 | 320 | ND | ND | 1.1 | 0.1 | 8.5 | 4.3 | 1.5 | 39.6 | 36.0 | 7.8 | 1.0 |
| | | 350 | 0.1 | 0.1 | 0.9 | 0.1 | 10.9 | 10.4 | 2.0 | 42.9 | 30.9 | 1.6 | 0.3 |
| | | 400 | 0.1 | 0.1 | 0.6 | ND | 12.4 | 19.8 | 1.9 | 46.8 | 17.9 | 0.3 | 0.1 |
| 8 | 8 | 280 | ND | ND | 0.8 | ND | 3.5 | 0.9 | 0.5 | 26.7 | 36.0 | 26.5 | 4.6 |
| | | 320 | ND | ND | 1.9 | ND | 6.7 | 11.8 | 0.8 | 49.8 | 27.2 | 0.7 | 0.3 |
| | | 425 | ND | ND | 0.9 | 0.2 | 5.5 | 25.7 | 0.7 | 59.1 | 5.9 | 0.1 | 0.2 |
| 9 | 9 | 280 | ND | ND | 0.3 | ND | 2.9 | 0.4 | 0.6 | 20.2 | 47.3 | 25.9 | 1.9 |
| | | 320 | ND | ND | 0.3 | ND | 3.8 | 1.4 | 1.0 | 29.3 | 48.4 | 14.3 | 1.1 |
| | | 425 | ND | ND | 0.3 | ND | 5.1 | 12.8 | 1.4 | 50.8 | 28.1 | 0.6 | 0.2 |
| Comp. Ex 1 | | 320 | 12.4 | ND | 0.2 | 2.4 | 30.3 | 18.0 | ND | 34.5 | ND | ND | ND |

ND = Not Detected

Examination of the data in Examples 1-3 above show that the amount of $CF_3CCl_2CF_3$ and $CF_3CClFCClF_2$ relative to $CF_3CCl_2CClF_2$ and $CF_3CClFCCl_2F$ can be increased by controlling the operational variables by using the catalysts of this invention. The $CF_3CCl_2CF_3$ and $CF_3CClFCClF_2$ produced above may be hydrogenated to $CF_3CH_2CF_3$ and $CF_3CHFCHF_2$ respectively using a palladium on carbon catalyst in accordance with the teachings of U.S. Pat. No. 5,523,501. The $CF_3CH_2CF_3$ and $CF_3CHFCHF_2$ may then be dehydrofluorinated to $CF_3CH\!=\!CF_2$ and $CF_3CF\!=\!CHF$, respectively, in accordance with the teachings of U.S. Pat. No. 6,369,284. $CF_3CH\!=\!CF_2$ and $CF_3CF\!=\!CHF$ may be recovered using procedures well known to the art.

What is claimed is:

1. A process for the manufacture of 1,1,3,3,3-pentafluoropropene and 1,2,3,3,3-pentafluoropropene comprising:

(a) reacting HF and at least one halopropene of the formula $CX_3CCl=CClX$, wherein each X is independently selected from the group consisting of F and Cl, to produce a product produce a product comprising $CF_3CCl_2CF_3$ and $CF_3CClFCClF_2$, wherein said $CF_3CCl_2CF_3$ and $CF_3CClFCClF_2$ in the presence of a chlorofluorination catalyst comprising at least one chromium-containing component selected from (i) a crystalline alpha-chromium oxide where at least 0.05 atom % of the chromium atoms in the alpha-chromium oxide lattice are replaced by divalent copper, and (ii) a chromium-containing composition of (i) which has been treated with a fluorinating agent;

(b) reacting $CF_3CCl_2CF_3$ and $CF_3CClFCClF_2$ produced in (a) with hydrogen, optionally in the presence of HF, to produce a product comprising $CF_3CH_2CF_3$ and $CF_3CHFCHF_2$ (c) dehydrofluorinating $CF_3CH_2CF_3$ and $CF_3CHFCHF_2$ produced in (b), to produce a product comprising $CF_3CH=CF_2$ and $CF_3CF=CHF$ and, (d) recovering $CF_3CH=CF_2$ and $CF_3CF=CHF$ from the product produced in (c).

2. The process of claim 1 wherein the amount of copper relative to the total of chromium and copper in the catalyst composition is from about 1 atom % to about 5 atom %.

3. The process of claim 1 wherein in (c), $CF_3CH_2CF_3$ and $CF_3CHFCHF_2$ are dehydrofluorinated in the vapor phase in the absence of a catalyst.

4. The process of claim 1 wherein in (c), $CF_3CH_2CF_3$ and $CF_3CHFCHF_2$ are dehydrofluorinated with caustic.

* * * * *